United States Patent [19]

Finkelmeier et al.

[11] Patent Number: 4,523,023
[45] Date of Patent: Jun. 11, 1985

[54] PREPARATION OF ISOCHROMANE DERIVATIVES

[75] Inventors: Horst Finkelmeier; Rudolf Hopp, both of Holzminden, Fed. Rep. of Germany

[73] Assignee: Haarmann & Reimer GmbH, Holzminden, Fed. Rep. of Germany

[21] Appl. No.: 575,439

[22] Filed: Jan. 31, 1984

[30] Foreign Application Priority Data

Feb. 23, 1983 [DE] Fed. Rep. of Germany ....... 3306200

[51] Int. Cl.³ .................. C07D 311/78; C07D 311/02
[52] U.S. Cl. .................................... 549/385; 549/389; 549/398; 549/408
[58] Field of Search ................ 549/385, 389, 398, 408

[56] References Cited

U.S. PATENT DOCUMENTS

| | | | |
|---|---|---|---|
| 3,360,530 | 12/1967 | Heeringa et al. | 549/385 |
| 3,532,719 | 10/1970 | Theimer | 549/398 |
| 3,910,964 | 10/1975 | Sanders et al. | 549/385 |
| 3,978,090 | 8/1976 | Sanders et al. | 549/385 |
| 4,162,256 | 7/1979 | Sprecker et al. | 549/385 |
| 4,181,665 | 1/1980 | McCall | 549/385 |
| 4,265,818 | 5/1981 | Wiegers et al. | 549/385 |
| 4,301,076 | 11/1981 | Wiegers et al. | 549/385 |

FOREIGN PATENT DOCUMENTS

915811  7/1954  Fed. Rep. of Germany .

*Primary Examiner*—Nicky Chan
*Attorney, Agent, or Firm*—Sprung, Horn, Kramer & Woods

[57] ABSTRACT

A process for the preparation of an isochromane of the formula

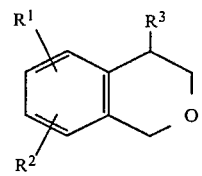

in which
$R^1$ and $R^2$ are identical or different and denote hydrogen, lower alkyl or lower alkoxy, or together form a cyclopentane or cyclohexane ring which is optionally substituted by lower alkyl and
$R^3$ denotes hydrogen or lower alkyl, comprising reacting an alcohol of the formula

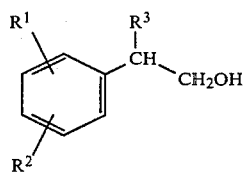

with formaldehyde and a carboxylic acid anhydride of the formula

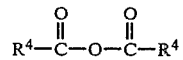

or with a methylene diester of the formula

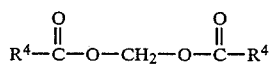

in which
$R^4$ represents a lower alkyl radical, in the presence of an acid catalyst. The products are known, having a musk-like odor.

6 Claims, No Drawings

PREPARATION OF ISOCHROMANE DERIVATIVES

The invention relates to a process for the preparation of isochromane derivatives.

It is known from Chem. Ber. 89, 1254 (1956) that isochromane can be prepared in a yield of 50% by reacting β-phenyl-ethyl alcohol with formaldehyde in the presence of hydrogen chloride.

German Offenlegungsschrift No. 1,951,001 describes the preparation of isochromanes by reacting an aromatic hydrocarbon with a lower alkylene oxide in the presence of aluminum chloride in order to prepare an aralkanol/aluminum chloride complex, then partially deactivating the aluminum chloride with a substance containing free hydroxyl groups, and finally adding formaldehyde in order to cyclize the aralkanol to an isochromane.

According to German Offenlegungsschrift No. 2,516,809, isochromanes can be prepared by reacting β-phenyl-ethyl alcohol with an acetal in the presence of proton acids.

The process gives isochromanes in unsatisfactory yields. In the process according to German Offenlegungsschrift No. 2,539,773, in which an azeotroping agent, such as n-hexane, cyclohexane, methylcyclohexane, benzene or toluene, is also added, working up is very expensive because of the azeotroping agent.

A process for the preparation of isochromane derivatives has been found, which is characterized in that alcohols of the formula (I)

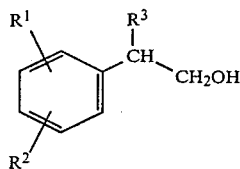

in which $R^1$ and $R^2$ are identical or different and denote hydrogen, lower alkyl or lower alkoxy, or together form a cyclopentane or cyclohexane ring which is optionally substituted by lower alkyl and $R^3$ denotes hydrogen or lower alkyl, are reacted with formaldehyde and a carboxylic acid anhydride of the formula (II)

in which $R^4$ represents a lower alkyl radical, or with a methylene diester of the formula (III)

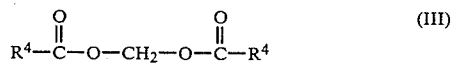

in which $R^4$ represents a lower alkyl radical, in the presence of an acid catalyst at elevated temperature.

Isochromanes can be prepared in high yields and in a simple manner by the process according to the invention.

The process according to the invention can be illustrated with the aid of the following equation:

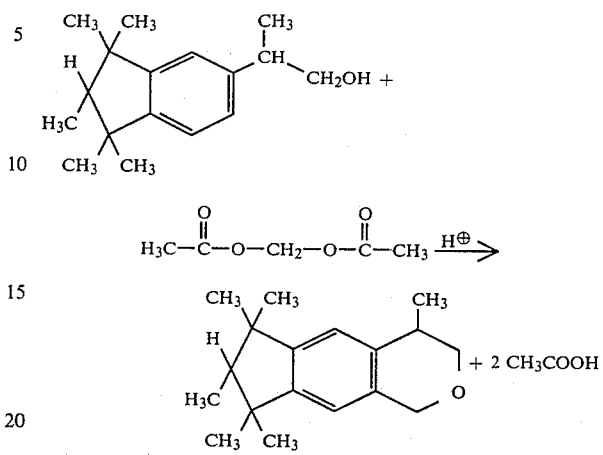

According to the invention, lower alkyl denotes a straight-chain or branched hydrocarbon radical with 1 to about 6 carbon atoms. The following lower alkyl radicals may be mentioned as examples: methyl, ethyl, propyl, isopropyl, butyl, isobutyl, pentyl, isopentyl, hexyl and isohexyl. Preferred lower alkyl radicals are the methyl, ethyl and isopropyl radicals.

According to the invention, lower alkoxy contains a straight-chain or branched hydrocarbon radical with 1 to about 6 carbon atoms in the alkyl part. The following lower alkoxy radicals may be mentioned as examples: methoxy, ethoxy, propoxy, isopropoxy, butoxy, isobutoxy, pentyloxy, isopentyloxy, hexyloxy and isohexyloxy. Preferred lower alkoxy radicals are the methoxy, ethoxy and isopropoxy radicals.

The radicals $R^1$ and $R^2$ can be linked to form a cyclopentane or cyclohexane radical. The cyclopentane or cyclohexane radical can be fused to the phenyl radical either in the 2,3- or in the 3,4-position. According to the invention, the cyclopentane or cyclohexane radical can preferably be substituted by lower alkyl groups, preferably by up to 6 and particularly preferably by 3 to 6 groups.

Preferred alcohols for the process according to the invention are compounds of the formula (IV)

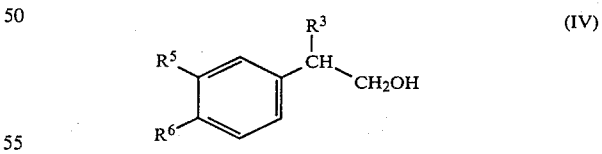

in which $R^5$ and $R^6$ each denote hydrogen or together form a cyclopentane or cyclohexane ring which is substituted by lower alkyl and $R^3$ has the abovementioned meaning.

Alcohols for the process according to the invention are known per se (German Auslegeschrift No. 1,287,242, German Auslegeschrift No. 2,219,953 and Japanese Pat. No. 53 031,635).

They can be prepared, for example, by reacting aromatics with a lower alkylene oxide ($C_1$ to about $C_6$) in the presence of aluminum chloride.

The formaldehyde for the process according to the invention is essentially paraformaldehyde.

Examples of carboxylic acid anhydrides for the process according to the invention are acetic anhydride, propionic anhydride, n-butyric anhydride, isobutyric anhydride, n-valeric anhydride, isovaleric anhydride and n-caproic anhydride. Acetic anhydride is the preferred anhydride.

Methylene diesters for the process according to the invention can be prepared by reacting paraformaldehyde with a carboxylic acid anhydride (Leibigs Ann. Chem. 402, 127 (1913)).

The preparation can be carried out, for example, by heating the reactants in the presence of catalytic amounts of an acid.

Examples of methylene diesters which may be mentioned are: methylene diacetate, methylene dipropionate, methylene di-n-butyrate, methylene diisobutyrate and methylene dicaproate.

Methylene diacetate is the preferred methylene diester.

Examples of suitable acid catalysts are acid clays, such as, for example, acid-doped montomorillonites, p-toluenesulphonic acid or ortho-phosphoric acid. Phosphoric acid or acid clays are the preferred acid catalysts for the process according to the invention.

The process according to the invention can be carried out in the temperature range from room temperature to 200° C. A temperature of 70° to 180° C. is preferred, and 100° to 150° C. is particularly preferred.

The process according to the invention can be carried out either under normal pressure or under increased pressure. A pressure range from normal pressure to 20 bar may be mentioned as an example. A pressure of 1.2 to 10 bar is preferred for the process according to the invention.

The process according to the invention can be carried out, for example, as follows: the reactants are introduced into an autoclave and are stirred at the reaction temperature. The carboxylic acid formed during the reaction is then distilled off. The reaction product is taken up in an organic solvent, such as toluene, and the mixture is neutralized or washed with alkaline aqueous solution, such as sodium hydroxide solution or sodium carbonate solution. The reaction product is distilled in vacuo. In the case of the acid clays, the catalyst is filtered off and the filtrate is distilled directly.

Isochromane derivatives of the formula (V)

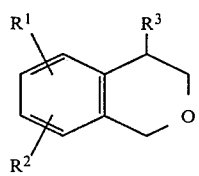

(V)

in which

R$^1$ to R$^3$ have the abovementioned meaning, can be prepared in the process according to the invention.

The following isochromanes may be mentioned as examples: 6-oxa-1,1,2,3,3,8-hexamethyl-2,3,5,6,7,8-hexahydro-1H-benz[f]indene (formula VI); 6-oxa-1,1,3,8-tetramethyl-3-ethyl-2,3,5,6,7,8-hexahydro-1H-benz[f]indene (formula VII); 6-oxa-1,3,3,8-tetramethyl-1-ethyl-2,3,5,6,7,8-hexahydro-1H-benz[f]indene (formula VIII); 6-oxa-1,1,2,3,3-pentamethyl-2,3,5,6,7,8-hexahydro-1H-benz[f]indene (formula (IX); 2-oxa-4,5,5,8,8-pentamethyl-1,2,3,4,5,6,7,8-octahydroanthracene (formula X); 2-oxa-5,5,8,8-tetramethyl-1,2,3,4,5,6,7,8-octahydroanthracene (formula XI); 6-oxa-1,1,2,8-tetramethyl-3-isopropyl-2,3,5,6,7,8-hexahydro-1H-benz[f]indene (formula XII); 6-oxa-2,3,3,8-tetramethyl-1-isopropyl-2,3,5,6,7,8-hexahydro-1H-benz[f]indene (formula XIII); 6-oxa-1,1,2-trimethyl-3-isopropyl-2,3,5,6,7,8-hexahydro-1H-benz[f]indene (formula XIV) and 6-oxa-2,3,3-trimethyl-1-isopropyl-2,3,5,6,7,8-hexahydro-1H-benz[f]indene (formula XV).

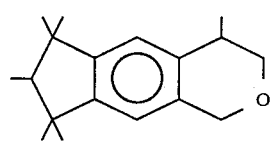

(VI)

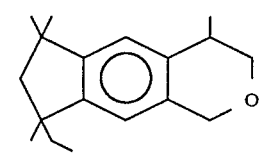

(VII)

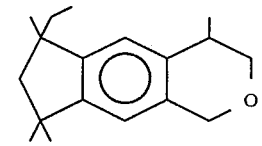

(VIII)

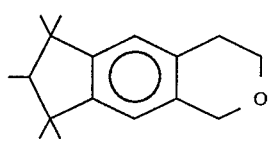

(IX)

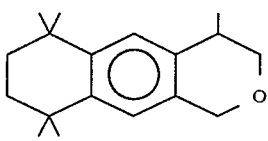

(X)

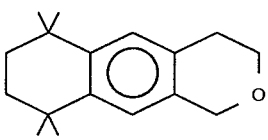

(XI)

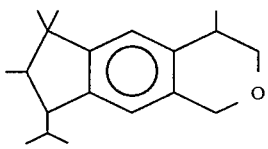

(XII)

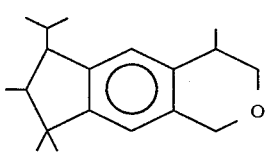

(XIII)

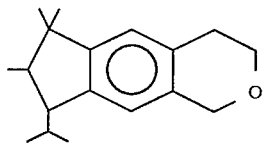 (XIV)

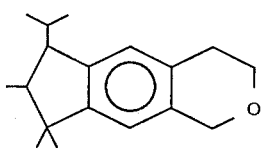 (XV)

The isochromanes according to the invention with fused-on polyalkylcyclopentane and polyalkylcyclohexane rings are high-quality musk aroma substances.

In the case where isochromanes without a fused-on cyclopentane or cyclohexane ring have been prepared by the process according to the invention, it is possible subsequently to introduce these rings in a second reaction step and thus also to obtain the musk aroma substances. Thus, isochromanes in which two adjacent carbon atoms in the phenyl ring are unsubstituted can be reacted with suitable dihalides, diols or dienes and the cyclopentane or cyclohexane ring can thus be fused-on (German Auslegeschrift No. 1,287,242, column 4, lines 12-48).

EXAMPLE 1

6-Oxa-1,1,2,3,3,8-hexamethyl-2,3,5,6,7,8-hexahydro-1H-benz[f]indene 94 g of acetic anhydride, 50 g of 85% strength phosphoric acid, 27.6 g of paraformaldehyde and 200 g of 2-(1',1',2',3',3'-pentamethyl-5'-indanyl)-1-propanol are successively added to an autoclave and the mixture is warmed to 135° C. The mixture is stirred at this temperature for 1 hour and the acetic acid formed is then distilled off. The mixture is then taken up in toluene and the organic phase is washed neutral with sodium hydroxide solution and water. The toluene is stripped off and the residue is distilled in vacuo. 179 g (85.3% of theory) of 6-oxa-1,1,2,3,3,8-hexamethyl-2,3,5,6,7,8-hexahydro-1H-benz[f]indene, which passes over under a pressure of 4 mbar at 155° to 160° C., are obtained.

EXAMPLE 2

(a) Methylene diacetate 5 g of concentrated sulphuric acid are added dropwise to a suspension of 300 g of paraformaldehyde in 1,020 g of acetic anhydride in the course of 5 minutes, during which the temperature rises from room temperature to about 100° C. When the addition had ended, the mixture is heated to 150° C. and is stirred at this temperature for 3 hours. It is then cooled to room temperature, 25 g of sodium acetate are added and the volatile constituents are distilled off in vacuo. About 1,300 g of distillate are thereby obtained, and are then fractionated, with addition of 10 g of sodium acetate, over a 50 cm packed column. 1,150 g (87.1% of theory) of methylene diacetate of boiling point 96° to 99° C. under 90 mbar are thereby obtained.

(b) 6-Oxa-1,1,2,3,3,8-hexamethyl-2,3,5,6,7,8-hexahydro-1H-benz[f]indene 200 g of 2-(1',1',2',3',3'-pentamethyl-5'-indanyl)-1-propanol, 50 g of 85% strength phosphoric acid and 122 g of methylene diacetate are introduced into an autoclave and the mixture is heated to 150° C., while stirring, for 1 hour. The mixture is worked up as in Example 1 to give 172 g (82.0% of theory) of 6-oxa-1,1,2,3,3,8-hexamethyl-2,3,5,6,7,8-hexahydro-1H-benz[f]indene.

EXAMPLE 3

(a) Methylene diacetate
See Example 2 (a).

(b) 6-Oxa-1,1,2,3,3,8-hexamethyl-2,3,5,6,7,8-hexahydro-1H-benz[f]indene 200 g of 2-(1',1',2',3',3'-pentamethyl-5'-indanyl)-1-propanol, 6.8 g of p-toluenesulphonic acid and 122 g of methylene diacetate are introduced into an autoclave and the mixture is heated to 130° C., while stirring, for 8 hours. The mixture is worked up as in Example 1 to give 167 g (79.6% of theory) of 6-oxa-1,1,2,3,3,8-hexamethyl-2,3,5,6,7,8-hexahydro-1H-benz[f]indene.

EXAMPLE 4

6-Oxa-1,1,2,3,3,8-hexamethyl-2,3,5,6,7,8-hexahydro-1H-benz[f]indene 200 g of 2-(1',1',2',3',3'-pentamethyl-5'-indanyl)-1-propanol are introduced into an autoclave and are warmed to 70° C. 50 g of 85% strength phosphoric acid are then added, followed by 27.6 g of paraformaldehyde. 120 g of propionic anhydride are then added dropwise. When the addition has ended, the autoclave is closed and the mixture is stirred at 140° C. for 5 hours. When the reaction has ended, the propionic acid formed is distilled off and the mixture is worked up as in Example 1. 171 g (81.5% of theory) of 6-oxa-1,1,2,3,3,8-hexamethyl-2,3,5,6,7,8-hexahydro-1H-benz[f]indene are obtained.

EXAMPLE 5

6-Oxa-1,1,3,8-tetramethyl-3-ethyl-2,3,5,7,8-hexahydro-1H-benz[f]indene and 6-oxa-1,3,3,8-tetramethyl-1-ethyl-2,3,5,6,7,8-hexahydro-1-H-benz[f]indene 200 g of a mixture of 2-(1',1',3'-trimethyl-3'-ethyl-5'-indanyl)-1-propanol and 2-(1',3',3'-trimethyl-1'-ethyl-5'-indanyl)-1-propanol (can be prepared by reacting propylene oxide with 1,1,3-trimethyl-3-ethylindane), 20 g of acid-doped montmorillonite (K10 catalyst, Süd-Chemie, Munich), 27.6 g of paraformaldehyde and 94 g of acetic anhydride are introduced into an autoclave and the mixture is heated to 150° C. for 5 hours. The mixture is allowed to cool to room temperature, the catalyst is filtered off, the acetic acid formed is stripped off and the residue is distilled in vacuo. 175 g (83.4% of theory) of a mixture of 6-oxa-1,1,3,8-tetramethyl-3-ethyl-2,3,5,6,7,8-hexahydro-1H-benz[f]indene and 6-oxa-1,3,3,8-tetramethyl-1-ethyl-2,3,5,6,7,8-hexahydro-1H-benz[f]indene are obtained.

EXAMPLE 6

2-Oxa-1,2,3,4-tetrahydro-naphthalene 94 g of acetic anhydride, 50 g of 85% strength phosphoric acid, 27.6 g of paraformaldehyde and 100 g of 2-phenyl-ethanol are introduced into an autoclave and the mixture is heated to 130° C. for 5 hours. The mixture is worked up as in Example 1 to give 89 g (81.0% of theory) of 2-oxa-1,2,3,4-tetrahydro-naphthalene of boiling point 55° C. under 1.7 mbar.

It will be appreciated that the instant specification and examples are set forth by way of illustration and not limitation, and that various modifications and changes may be made without departing from the spirit and scope of the present invention.

What is claimed is:

1. A process for the preparation of an isochromane of the formula

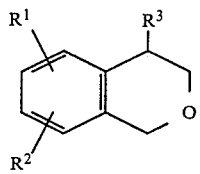

in which

R$^1$ and R$^2$ are identical or different and denote hydrogen, lower alkyl or lower alkoxy, or together form a cyclopentane or cyclohexane ring which is optionally substituted by lower alkyl and R$^3$ denotes hydrogen or lower alkyl, comprising reacting an alcohol of the formula

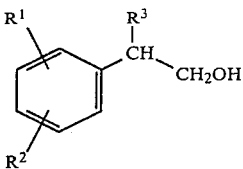

with formaldehyde and a carboxylic acid anhydride of the formula

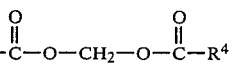

or with a methylene diester of the formula

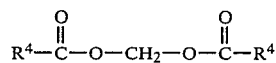

in which

R$^4$ represents a lower alkyl radical, in the presence of an acid catalyst.

2. A process according to claim 1, wherein the carboxylic acid anhydride comprises acetic anhydride.

3. A process according to claim 1, wherein the methylene diester comprises methylene diacetate.

4. A process according to claim 1, wherein the acid catalyst comprises orthophosphoric acid or an acid clay.

5. A process according to claim 1, wherein the process is carried out in the temperature range from about room temperature to about 200° C.

6. A process according to claim 5, wherein R$^4$ is methyl and the acid catalyst comprises orthophosphoric acid or an acid clay.

* * * * *